(12) United States Patent
McKown

(10) Patent No.: US 7,146,976 B2
(45) Date of Patent: Dec. 12, 2006

(54) NASAL CANNULA RETAINER

(76) Inventor: Joseph R. McKown, 1130 Elder Ave., Chesapeake, VA (US) 23325

( * ) Notice: Subject to any disclaimer, the term of this patent is extended or adjusted under 35 U.S.C. 154(b) by 0 days.

(21) Appl. No.: 10/357,050

(22) Filed: Feb. 3, 2003

(65) Prior Publication Data

US 2004/0025884 A1    Feb. 12, 2004

Related U.S. Application Data

(60) Provisional application No. 60/401,193, filed on Aug. 6, 2002.

(51) Int. Cl.
*A61M 16/00* (2006.01)
*A61M 15/08* (2006.01)
(52) U.S. Cl. .................. 128/200.24; 128/DIG. 26; 128/207.11; 128/207.18; 2/918
(58) Field of Classification Search ........... 128/200.24, 128/201.24, 204.18, 205.22, 207.17, 207.18, 128/DIG. 26
See application file for complete search history.

(56) References Cited

U.S. PATENT DOCUMENTS

| | | | | | |
|---|---|---|---|---|---|
| 3,683,907 | A | * | 8/1972 | Cotabish | 128/200.28 |
| 4,665,566 | A | * | 5/1987 | Garrow | 2/171 |
| 4,739,757 | A | * | 4/1988 | Edwards | 128/207.18 |
| 4,774,946 | A | * | 10/1988 | Ackerman et al. | 128/207.18 |
| 4,836,200 | A | * | 6/1989 | Clark | 128/207.18 |
| 5,117,818 | A | * | 6/1992 | Palfy | 128/204.11 |
| 5,400,776 | A | * | 3/1995 | Bartholomew | 128/200.24 |
| 5,645,058 | A | * | 7/1997 | Odom | 128/207.18 |
| 5,704,916 | A | * | 1/1998 | Byrd | 604/179 |
| 6,026,811 | A | * | 2/2000 | Settle | 128/207.17 |
| 6,298,850 | B1 | * | 10/2001 | Argraves | 128/207.17 |
| 6,450,166 | B1 | * | 9/2002 | McDonald et al. | 128/206.27 |
| 6,536,436 | B1 | * | 3/2003 | McGlothen | 128/207.18 |

* cited by examiner

*Primary Examiner*—Glenn K. Dawson
(74) *Attorney, Agent, or Firm*—David J. Bolduc

(57) ABSTRACT

A nasal cannula apparatus is provided for use by patients desiring a comfortable arrangement. The nasal cannula apparatus is particularly suited for long-term oxygen users, for extended wear in both standing, resting and supine positions. The nasal cannula apparatus has headgear and retainers for holding the gas supply tubes, which are adjustable to allow fast and easy adjustment to size. The headgear and retainers allow the cannula tubes to be held in a position which prevents skin discomfort and irritation, and which promotes healing of such irritation, injuries and sores.

14 Claims, 3 Drawing Sheets

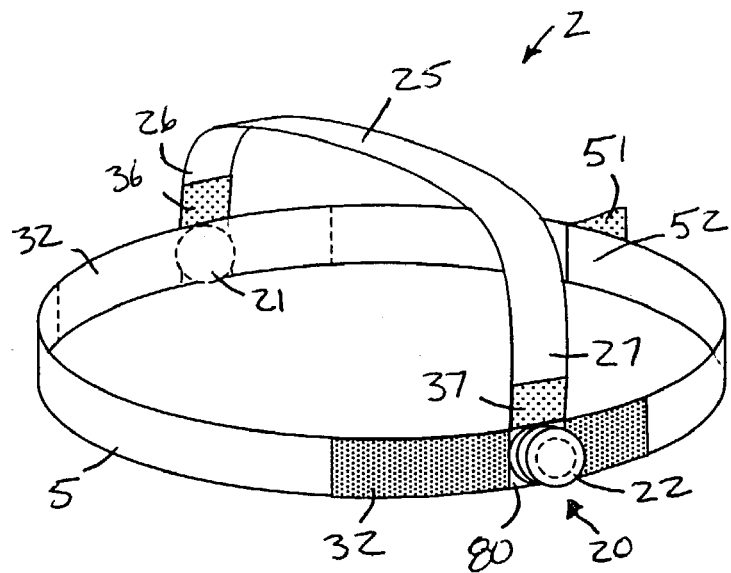
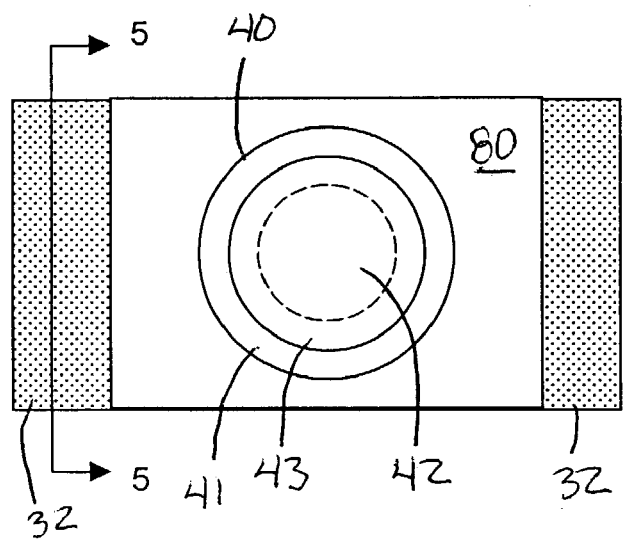
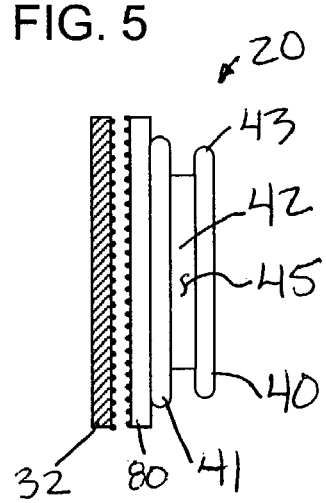
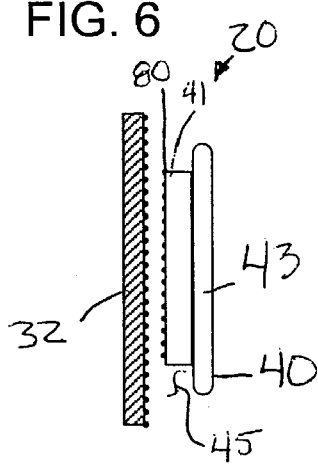

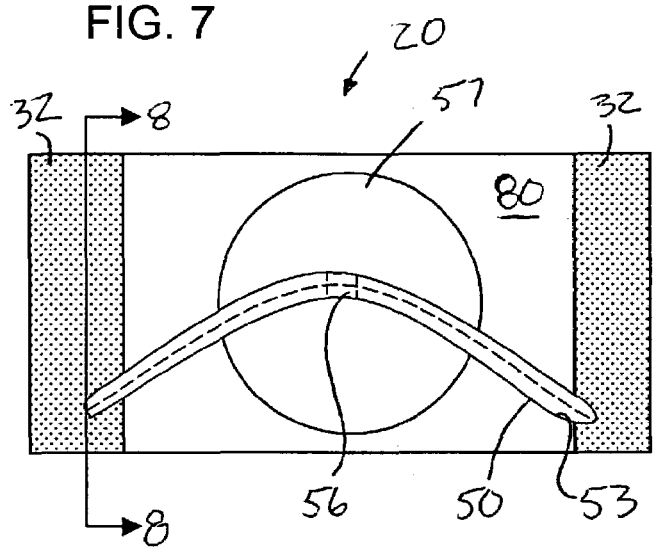
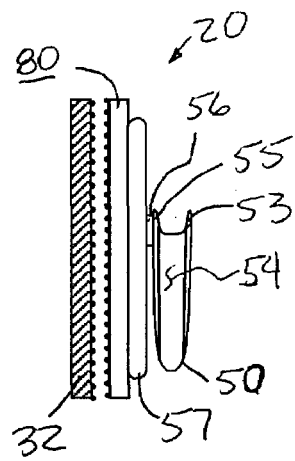
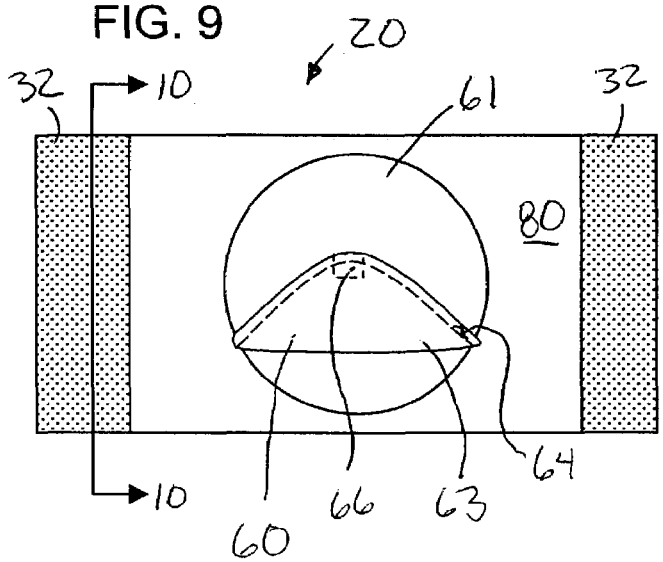
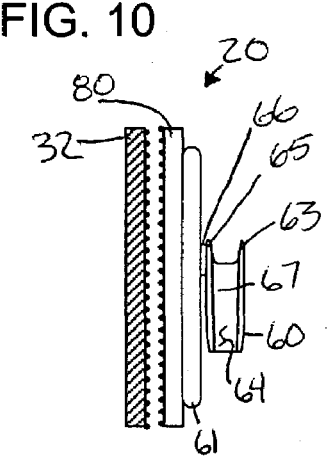
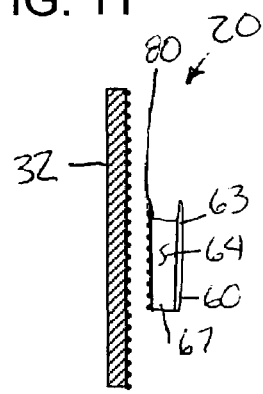

NASAL CANNULA RETAINER

The following application claims priority under 35 U.S.C. 119(e) of Provisional Application No. 60/401,193, filed Aug. 6, 2002

BACKGROUND OF THE INVENTION

1. Field of the Invention

The present invention relates to nasal cannula apparatus for use by patients, desiring a comfortable arrangement. The nasal cannula apparatus is particularly suited for long-term oxygen users, for extended wear in both standing, resting and supine positions. The nasal cannula apparatus has headgear and retainers for holding the gas supply tubes, which are adjustable to allow fast and easy adjustment to size. The headgear and retainers allow the cannula tubes to be held in a position which prevents skin discomfort, irritation, blisters, abrasions, pressure sores and other injuries and promotes healing of such irritation, injuries and sores.

2. Description of the Prior Art

There are a number of persons requiring supplemental oxygen such as after surgery to aid in the healing process, and persons having lungs of limited capacity due to disease or lung damage which require supplemental oxygen to assist in everyday life. These people having respiratory problems are typically assisted in breathing by providing a gas source, which provides pressurized ambient or oxygen enriched air to the lungs of the patient via a nasal cannula. A typical arrangement for a cannula apparatus is illustrated in U.S. Pat. No. 3,726,275, Jackson et al., entitled "Nasal Cannulae". The nasal cannula comprises essentially a nasal assembly, or nosepiece, with a hollow main body having two directed orifices near or in a patient nostrils. Typically, the orifices consist of nasal extension tubes extending upwardly from a main body portion and gas is supplied through supply tubes to the main body, which acts as a distributing manifold. Commonly, the cannula nosepiece is held in place by extending the gas supply tubes from the patient's nasal area to behind the patient's ears. The flexible tubes are bent downward behind the ears to run along the jaw area, and are held in place by an adjustable slip loop or a cinch tightened below the chin to hold the nosepiece in place. Oxygen or other gas flows through the tubes to the two orifices, thereby supplying the patient with pressurized ambient or oxygen enriched air.

While being one of the most convenient methods known to date for supplying a patient with a gas enriched environment, existing nasal cannulae suffer a major drawback: the positioning of the tubes around the ears for support is uncomfortable and can cause the patient chaffing and pain. Additionally, existing nasal cannulae are prone to falling off the patient's face. Patients regularly find that body movement, especially during sleep, causes the cannula to dislocate, depriving the patient of the needed oxygen enrichment. Accidental removal of the cannula can also cause severe discomfort to the patient and in certain cases may even be life threatening.

As a means of preventing movement of the cannula from within the nasal passages of the patient, numerous devices are known to the prior art for stabilizing the cannula with respect to the patient. Some devices employ the gas supply tubes that supply air from the respirator to the cannula for holding the cannula in place. For example, in U.S. Pat. No. 3,915,173 to Brekke, a cannula assembly is shown wherein portions of the gas supply tubes are seated on the bridge of the patient's nose. In U.S. Pat. No. 2,693,800, the gas supply tubes are passed over the ears of the patient.

U.S. Pat. No. 2,168,705, Francisco et al., entitled "Nasal Inhaler", discloses a support for cannula tubes having temples which clasp behind the wearer's ears and include nose pads of the type used with eyeglasses. The use of temples and nose pads also makes this arrangement uncomfortable and not well suited for use while the wearer is sleeping.

U.S. Pat. No. 2,259,817, Hawkins, entitled "Adjustable Head Attachment for Oxygen Tubes" discloses a support for cannula tubes having an adjustable temple band and an adjustable crown band These bands and associated buckles, together with the obtrusive nose portion of the cannula tube also make this arrangement uncomfortable and unsuitable for sleeping.

U.S. Pat. No. 4,559,941, Timmons et al, entitled "Eyeglass Frame and Nasal Cannula Assembly", discloses a cannula apparatus which supports and substantially conceals the cannula tubes by eyeglass frames. That arrangement is not well suited for use while the wearer is sleeping. In addition, some individuals who do not wear glasses for reasons of vision find glasses uncomfortable or awkward and would prefer another nasal cannula arrangement.

U.S. Pat. No. 4,808,160 to Timmons, et al discloses a "Nasal Cannula Apparatus" comprising a headband with a cannula junction thereon from which nasal tubes extend downwardly across the face on either side of the nose, and curve up into the nostrils. This arrangement is uncomfortable against the face and can block or impair ones vision.

U.S. Pat. No. 4,774,946 to Ackerman, et al discloses a "Nasal and Endotracheal Tube Apparatus" for use with infants comprising bulbous nasal tubes and a headband yoke for clipping corrugated supply tubes thereto. This arrangement is uncomfortable in the nasal passages and is not compatible with standard supply tubes.

U.S. Pat. No. 4,367,735 to Dali discloses a "Nasal Cannula" with ribbed nose prongs attached to a foam base for attachment to a skullcap. The foam base, which extends across the face is bulky and can also be uncomfortable as well as obstructive.

U.S. Pat. No. 4,699,139 to Marshall, et al, U.S. Pat. No. 4,949,733 to Sampson, U.S. Pat. No. 5,400,776 to Bartholomew, and U.S. Pat. No. 6,026,811 to Settle, all teach devices that fit around the supply tubes and are placed on or around a patients ears. These devices are used to maintain a bend in a tube and/or provide padding for comfort about the ears. U.S. Pat. No. 6,434,796 to Speirs also teaches an "Oxygen Delivery Cannula Retainer, Cannula With Retainers Assembly, And Method For Retaining Cannulas" comprising a device securable about a patients ears. Although meant to provide comfort, these devices still create chaffing and discomfort due to placement about the patient's ears.

U.S. Pat. No. 5,636,630 to Miller et al., U.S. Pat. No. 4,836,200 to Clark, U.S. Pat. No. 4,422,456 to Tiep, and U.S. Pat. No. 6,298,850 to Argraves, all attempt to solve this problem. Miller et al. discloses running the tubes behind the patient head and utilizing a coupling portion contacting the back of the head, with the gas conduits passing in criss-cross manner behind the head. This arrangement suffers from several disadvantages, major amongst them is the location of both oxygen tubes behind the patient's head where they may be blocked if the head is resting thereupon. Additionally, placement of tubes behind the head is often uncomfortable to the patient.

The Clark patent utilizes a pressure-fastening strap adapted to go over the top of a user's head, onto which the flexible tubes are attached. Clark's preferred implementation is less desirable since the strap may slide over the head of the user and is liable to entangle with the patient's hair.

Tiep and Argraves disclose means for supporting the cannula in place by an elastic band that is adjustably connected to two holders each located on one of the conduits or flexible tubes. An elastic band extending behind the patient's head is secured to the tubes. A problem with these inventions is that the elastic band runs the risk of entanglement in the patient's hair.

The major problem with the cannulas and retainers of the prior art is that they rub on the face and ears of a patient under extended use. This rubbing causes discomfort, chaffing, sores and infections, particularly in elderly patients and other with heightened sensitivity such as chemotherapy patients. The retainers and pads of the prior art are also obtrusive, uncomfortable and unattractive and do not particularly alleviate the chaffing of the skin of the face and ears.

Another major problem with such prior art cannula occurs when the main oxygen delivery tube which delivers oxygen to the cannula gets snagged on an object, which happens frequently during the course of a day for a mobile person such as when carrying or pulling a portable oxygen tank or a person connected by a long main tube to a stationary oxygen concentrator located in a house or apartment. When such snagging occurs, the oxygen tubes are typically pulled downwardly such that the tension on the upper portions of the oxygen tubes is significantly increased jamming the nosepiece into the person's nose causing much discomfort to such person and potential injury to the nose, ears, and face of the person. Such snagging also causes the upper portions of the respective oxygen tubes to move upwardly towards the person's eyes partially blocking the field of view, which can be particularly hazardous while driving an automobile.

Another problem is that the retaining collars are prone to slip downwardly during cannula use such that the tension on the oxygen tubes is reduced. Such loss of tension can cause the nosepiece to fall from the person's nose and the oxygen tubes to fall from around the person's ears. This is particularly prone to occur when the person is asleep and is typically caused by tossing and turning of the person causing contact of the cannula and retaining collar against the bed. The person generally awakes when the nosepiece dislodges or falls from the person's nose due to the insufficient supply of oxygen to the person's brain, and the person must subsequently reattach the cannula. This activity disrupts the person's sleep particularly when occurring multiple times each night. If the person does not awake, potentially serious hypoxia, including permanent brain damage and death can occur due to the lack of sufficient oxygen supply to the person's brain.

Thus, there is a need for a means and method for retaining a cannula in place during use, to particularly prevent the chaffing of the ears and face, and for preventing painful tugging on the oxygen tubes jamming the nose piece into the person's nose, particularly while the person is awake and active.

It is clear therefore that a need exists for a device to secure a nasal cannula to a patient's head in a light, inexpensive, and effective manner, and doing so in a manner that will be unobtrusive to the patient. Additionally, a better solution is needed for providing user comfort in the nasal septum and other facial areas as described above. The current invention discloses such a device and method for its use.

SUMMARY OF THE INVENTION

According to the present invention, there is provided a cannula retainer that keeps the cannula off of the ears and face of the patient, thereby eliminating skin irritation caused by other cannulas and retainers. The disclosed invention retains the cannula supply tubes on holders mounted to a headpiece such as a hat, cap or headband. The holders comprise a pair of grooved retainers that are adjustably attached to the headpiece. The headpiece or cap is also adjustable in order to fit a variety of head sizes.

The preferred embodiment of the invention provides an adjustable cap having hook and loop fastener material affixed thereto. The hook and loop fasteners may be engaged and disengaged from the grooved round dowels also having hook and loop fasteners affixed thereto, thereby providing a means for attachment and adjustment of the retainers on the cap or headpiece. The cannula tubes are placed on the retainers and are held thereon in the grooves and tend from the retainers such that they do not rub on the patient's ears or face. Thus, the cap and retainers may be adjusted to a position suitable for a patient's head size and/or position of comfort for the cannula tubes.

Its is therefor an object of the present invention to provide a cannula retention apparatus that provides a comfortable retainer for a cannula, and minimizes discomfort of the patient wearing the cannula.

It is another object of the present invention to provide a device of the character described wherein the cannula supply tubes are not positioned around the ears for support.

It is another object of the present invention to provide a device of the character described that is not prone to falling off the patient's face.

It is another object of the present invention to provide a device of the character described wherein the cannula does not cause the patient chaffing or pain.

It is another object of the present invention to provide a device of the character described wherein the patient's body movement does not cause the cannula to dislocate.

It is another object of the present invention to provide a device of the character described wherein the cannula tubes are not seated on the bridge of the patient's nose or other parts of the face.

It is another object of the present invention to provide a device of the character described wherein the tube or retainers do not block or impair ones vision.

It is another object of the present invention to provide a device of the character described wherein foam or base does not extend across the face.

It is another object of the present invention to provide a device of the character described which is not bulky or obstructive.

It is another object of the present invention to provide a device of the character described which does not secure behind the head.

It is another object of the present invention to provide a device of the character described wherein the tubes may not be blocked by the head in resting position.

It is another object of the present invention to provide a device of the character described wherein the retainer or tubes are not liable to entangle with the patient's hair.

It is another object of the present invention to provide a device of the character described wherein that does not rub on the face and ears of a patient under extended use.

It is another object of the present invention to provide a device of the character described wherein the device does not cause discomfort, chaffing, sores and infections, particularly in elderly patients and other with heightened sensitivity such as chemotherapy patients.

It is another object of the present invention to provide a device of the character described wherein the cannula is not prone to snagging on objects.

It is another object of the present invention to provide a device of the character described wherein the tension on the upper portions of the oxygen tubes is controllable.

It is another object of the present invention to provide a device of the character described wherein the controlling tension of the device prevents jamming of the nosepiece into the person's nose.

BRIEF DESCRIPTION OF THE DRAWINGS

The above and other objects and advantages of the present invention will be apparent upon consideration of the following detailed description, taken in conjunction with accompanying drawings, in which like reference characters refer to like parts throughout, and in which:

FIG. 3 is a perspective view of an alternate adjustable headpiece configuration for the cannula retainer;

FIG. 4 is a plan view of an adjustable retaining dowel as in FIG. 3;

FIG. 5 is an elevation view of the adjustable retaining dowel of FIG. 4, having a central groove therein;

FIG. 6 is an elevation view of an alternate adjustable retaining dowel as in FIG. 4, having a proximal groove therein;

FIG. 7 is a plan view of an alternate adjustable retainer;

FIG. 8 is an elevation view of an alternate adjustable retainer as FIG. 7;

FIG. 9 is a plan view of an another alternate adjustable retainer;

FIG. 10 is an elevation view of the adjustable retainer of FIG. 9, having a central groove therein; and FIG. 11 is an elevation view of the adjustable retainer of FIG. 9, using direct attachment of fasteners to the proximal face of the retainer.

DESCRIPTION OF THE PREFERRED EMBODIMENT

Figure 1:
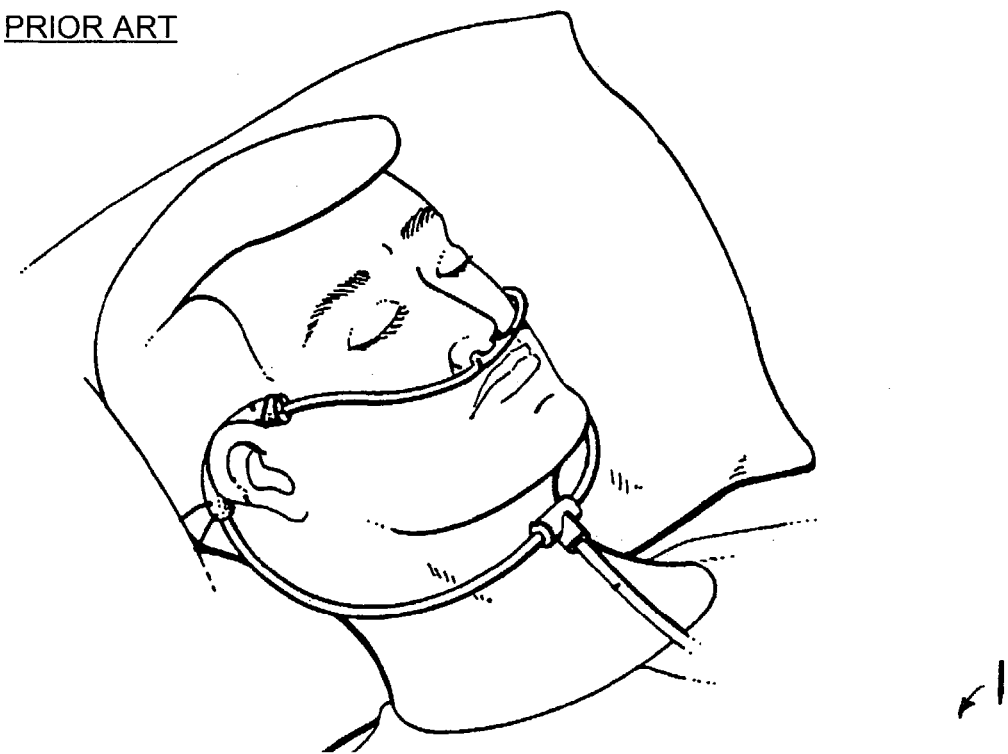
FIG. 1 is a perspective view of a cannula with ear pads of the prior art.

The present invention provides an apparatus for retention of a nasal cannula. The nasal cannula comprises essentially a nasal assembly 18, or nosepiece, with a hollow main body 15 having two directed orifices 16, 17 near or in a patient nostrils. The orifices consist of nasal extension tubes 16, 17 extending upwardly from a main body portion 15 and gas is supplied through supply tubes 11, 12 to the main body 15, which acts as a distributing manifold to the extension tubes 16, 17. Oxygen or other gas flows through the tubes 11, 12 to the two orifices 16, 17, thereby supplying the patient with pressurized ambient or oxygen enriched air.

In the prior art, the cannula nosepiece 18 is held in place by extending the gas supply tubes 11, 12 from the patient's nasal area behind the patient's ears. The flexible tubes 11, 12 are bent downward behind the ears to run along the jaw area, and are held in place by an adjustable slip loop or a cinch 13 tightened below the chin to hold the nosepiece 18 in place.

In the present invention, the cannula nosepiece 18 is held in place instead by extending the gas supply tubes 11, 12 from the patient's nasal area to the supply tube retainers 21, 22 mounted above the patient's ears on a hat, cap, headband, headpiece 1 or the like. The flexible tubes 11, 12 are bent downward around the grooved retainers 21, 22 to run downwardly, and may be held in place by an adjustable slip loop or a cinch 13 tightened below the chin to hold the nosepiece 18 in place. Preferably, the tubes 11, 12 are extended from the nosepiece 18, and a loop is formed tending behind and around grooves the retainers 21, 22, then downwardly towards the tube junction 14 and cinch 13. This provides a secure holding point for each supply tube 11, 12, not only from the friction provided by each groove against each tube 11, 12, but also from the friction of the contact between the tubes 11, 12 in the looped portion of below the retainers 21, 22. Alternately, the tubes 11, 12 may be extended from the nosepiece 18, and tend from the front to the back around the grooves the retainers 21, 22, then downwardly towards the tube junction 14 and cinch 13.

Figure 2:
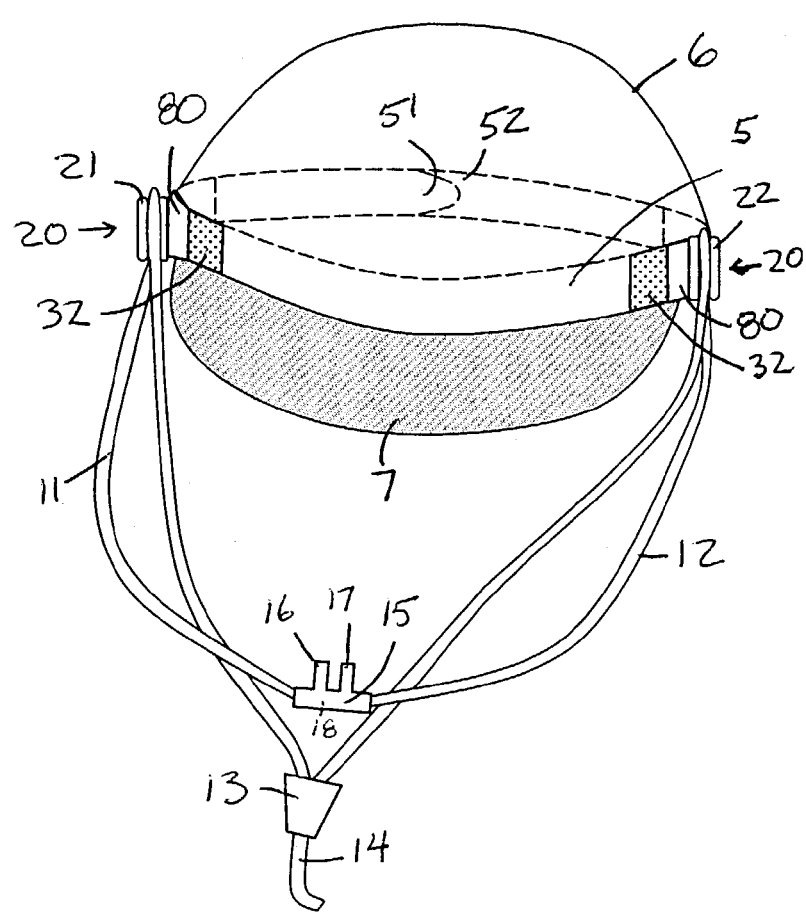
FIG. 2 is a perspective view of one embodiment of the cannula and retainer of the present invention.

Referring to FIG. 2: In the preferred embodiment of the invention, the cannula retention apparatus comprises a type of hat 1 or headgear 1 that a person can comfortably wear on their head. The embodiment in FIG. 2 shows a typical baseball type cap 1. The cap 1 comprises an adjustable headband 5 having a crown portion 6 affixed thereto. The headband 5 adjusts to fit the radius of the person's head and the crown 6 provides material covering the top of the head surrounded by the headband 5. The crown portion 6 essentially covers the head while providing a means of preventing the headband 5 from slipping lower on the head. The crown portion 6 may be made of typical hat materials including cotton, polyester, nylon, felt, straw, plastic, paper or other material appropriate to the type of hat construction. The baseball style of cap 1 (as well as other types) also generally has a visor 7 attached to the front portion of the headband 5 and crown 6 and provides a means of keeping sunlight out of ones eyes.

The headband 5 may be adjustable to fit a variety of head sizes. The adjustable headband 5 is preferably constructed from an elasticized material. Further adjustability may be provided by using hook and loop fasteners (VELCRO), snaps, eyelets, laces, buckles or other conventional fasteners. For elasticized embodiments of the headband 5, the elasticized material may comprise any portion of or the entirety of the headband 5. For the other types of fasteners, these fasteners are preferably located at the rear of the headband 5, opposite the visor 7. Complimentary fasteners at the rear of the headband 5 are preferably located on detachable/attachable ends 51, 52 of the headband 5 to provide the adjustment capability.

Wherein the embodiment of the invention shown in FIG. 2 illustrates a baseball type of cap 1, many other types of headgear 1 are envisioned for use in the cannula retainer, including but not limited to: hats for men, women, or children; hospital caps; golf caps; tennis caps; fishing hats; western hats; men's and women's dress hats, derbies; fedoras; bonnets; helmets; construction hard hats; straw hats; visor-less caps; berets; winter hats; and any variety of hats on or within which retainers 20 may be attached.

Referring again to FIG. 2: The cannula retention assembly further comprises retainers 20 which in this embodiment comprise a pair of dowels 21, 22 attached to the headband 5 of the cap 1. The dowels 21, 22 may be attached by pop riveting, gluing, sewing, screwing or otherwise to the headband 5 and or crown 6 of the cap 1. In the most preferable embodiment of the invention, the dowels 21, 22 are connected to the cap 1 using hook and loop fasteners (such as VELCRO). For example, a length loop fastener material 32 may be sewn or glued to the headband 5 and/or crown 6 of the cap 1, while the dowels 21, 22 may be attached to a segment of hook material 80. This allows the dowels 21, 22 to be placed anywhere along the length of loop material 32, which provides the ability to adjust the dowels' 21, 22 placement to one's preferences. The hook material 32 may extend around the whole circumference of the headband 5 to maximize adjustability of the dowels 21, 22. However, in the preferred embodiment of the invention a first length of loop (or hook) 32 material is sewn or glued from the right edge of the visor 7 around the headband 5 to the area of the headband 5 just behind the right ear. Likewise, a second length of loop (or hook) material 32 is sewn or glued from the left edge of the visor 7 around the headband 5 to the area of the headband 5 just behind the left ear.

Referring now to FIGS. 4–6: The retainers 20 comprising dowels 21, 22 are preferably constructed so as to retain supply tubes 11, 12 and a nasal cannula nosepiece 18 therebetween, and to be adjustable as to their location on the headband 5 or crown 6 of the cap 1. Since dowels 21 and 22 are essentially identical, the description herein of the first dowel 22 applies equally to the second dowel 21, and for simplicity is identified as dowel 40 in the FIGS. 4–6. The dowel 40 preferably comprises a rounded structure with a groove 45 therein, which is adapted to retain a cannula supply tube 11 or 12 therein, without bending or blocking the tube 11, 12. In the embodiment of the dowel 40 of FIGS. 4–6, the dowel 40 comprises a cylindrical block of material. The cylindrical block may be constructed from wood, plastic, metal, leather, rubber, cardboard, foam rubber, resilient Styrofoam, polystyrene or any material sufficiently rigid to support the supply tubes 11 or 12 and cannula nosepiece 18 therebetween. To maximize comfort to the wearer and provide a more secure attachment point to the cap 1, the dowels 40 are preferably constructed of a light and rigid material such as foam rubber, which is not only light, but also simplifies assembly because of the ability to easily fabricate a dowel using a punch. The diameter of the cylinder is preferably between 0.5–2.0 inches to provide a light dowel 40 that has a sufficient diameter to preclude bending of a cannula tube 11, 12 supported thereby. The height of the cylinder is at least as wide as the diameter of a standard cannula tube 11, 12 and preferably at least twice as wide as the cannula tube 11, 12 diameter, or approximately 0.3–1.0 inches.

The cylindrical dowel 40 also has a circumferential groove 45 therein. The groove 45 may be centered between the proximal 41 and distal 43 circular portions of the dowel 40 as in FIG. 5, but is preferably located at the proximal side 41 of the dowel 40 as in FIG. 6. The depth of the groove 45 must be sufficient to retain a cannula tube 11, 12 therein. More preferably, the depth of the groove 45 is at least half the diameter of the cannula supply tube 11, 12 and up to 3 times the tube 11, 12 diameter, or approximately 0.1–0.6 inches.

In the preferred embodiment of the invention, the dowel 40 is are of unitary construction. However, in an alternate embodiment of invention, the dowel 40 may be constructed with two or more modules 41, 42, 43 that are attached together. This may be accomplished using two disks 41, 43 having a first circumference, and attaching the two outer disks 41, 43 to the opposing faces of a third disk 42 having a smaller circumference. This creates a modular dowel 40 having a first circumference, with a central circumferential groove 45 having a smaller circumference than the proximal 41 and distal 43 outer portions of the modular dowel 40 as in FIG. 5. Preferably, the dowel 40 is constructed using a disk 43 having a first circumference, and attaching the disk 43 to the third disk 42 which has a smaller circumference. This creates a modular dowel 40 having a first circumference, with a circumferential groove 45 on the proximal portion 41 of the dowel 40 having a smaller circumference than distal 43 outer portion of the modular dowel 40 as in FIG. 6.

Referring to FIGS. 4 and 5: In one embodiment of the dowel 40, the face of the proximal portion 41 of the cylindrical dowel 40 is affixed to one face of a length of hook (or loop) fastener material 80. The dowel 40 is attached to the back face of the hook or loop material 80, i.e., the face of the material opposite to the attachment point of the dowel 40 has the hook or loop fasteners thereon. This attachment may be accomplished by gluing, sewing, riveting or like attachment methods. This allows the dowel 40 and attached hook or loop fastener material 80 to be attached to the loop or hook material 81 along the headband 5 or crown 6 of the cap 1. Alternatively, the dowel 40 may be attached directly to the cap 1 by sewing, gluing, riveting or other attachment methods.

Referring now to FIGS. 4 and 6: In the preferred embodiment of the dowel 40, the face of the proximal grooved portion 42 of the cylindrical dowel 40 is affixed to one face of a length of hook (or loop) fastener material 80. The dowel 40 is attached to the back face of the hook or loop material 80, i.e., the face of the material opposite to the attachment point of the dowel 40 has the hook or loop fasteners thereon. This attachment may be accomplished by gluing, sewing, riveting or like attachment methods. This allows the dowel 40 and attached hook or loop fastener material 80 to be attached to the loop or hook material 81 along the headband 5 or crown 6 of the cap 1. Alternatively, the dowel 40 may be attached directly to the cap 1 by sewing, gluing, riveting or other attachment methods.

Referring now to FIGS. 7–8: An alternate retainer assembly 20 for the supply tubes 11, 12 comprises a pair of grooved arc retainers 50 which may similarly be affixed to the material 81 on the headband 5 or crown 6 of the cap 1. The arced retainers 50 are preferably constructed so as to retain supply tubes 11, 12 and a nasal cannula nosepiece 18 therebetween, and to be adjustable as to their location on the headband 5 or crown 6 of the cap 1. Each arced retainer 50 preferably comprises an arced structure 50 with a groove 54 therein, which is adapted to retain a cannula supply tube 11, 12 therein, while maintaining a bend in the tube 11, 12. In the embodiment of the retainer 50 of FIGS. 6 and 7, each arced retainer 50 comprises a bent length of material 50. The retainer 50 may be constructed from wood, plastic, metal, leather, hard rubber, or any material sufficiently rigid to support the supply tubes 11, 12 and cannula nosepiece 18 therebetween. To maximize comfort to the wearer and provide a more secure attachment point to the cap 1, the dowels 50 are preferably constructed of a light and rigid material such as plastic. The thickness of the material is preferably between 0.2 to 0.5 inches to provide a light retainer 50. The arc preferably has a length and a radius of curvature sufficient to preclude kinking and blocking of a cannula tube 11, 12 supported thereby. The length of the arc may vary from between 0.5 inches to up to 3 inches, and the radius of curvature may be as few as 1 inch or as much as 10 inches. In the most preferred embodiment, the length of the arc is approximately 1.5 inches with a radius of curvature of 4 inches. The width of the arced retainer is at least as wide as the diameter of a standard cannula tube and preferably at least twice as wide as the cannula tube diameter, or approximately 0.3–1.0 inches.

The arced retainer 50 also has a groove 54 along the top portion of the retainer 50, preferably centered in the width dimension between the proximal 55 and distal 53 portions of the retainer 50. The depth of the groove 54 must be sufficient to retain a cannula tube 11, 12 therein. More preferably, the depth of the groove 54 is at least half the diameter of the cannula supply tube 11, 12 and up to 3 times the tube diameter, or approximately 0.1–0.4 inches.

On the central portion of the proximal portion 55 of each arced retainer 50 is a connection point 57 for securing the retainer 50 to one face of a length of hook (or loop) fastener material. The connection point 57 is attached to the back face of the hook or loop material 80, i.e., the face opposite to the attachment point 57 of the retainer 50 has the hook or loop fasteners thereon. In FIGS. 6 and 7, this connection point is shown as a flat disc 57 with a small cantilever 56 that connects at the central portion of the arced retainer 50. The attachment point 57 however may comprise shapes other than a disc, such as a square, and the cantilever 56 may be eliminated. With the cantilever 56 eliminated, the arced retainer 50 may be connected at more than one point to the disc 57. The attachment between the arced retainer 50, cantilever 56, disk 57 and fastener 80 may be accomplished by gluing, sewing, riveting, snaps or like attachment methods. This allows the retainer 50 and attached hook or loop fastener material 80 to be attached to the loop or hook material 81 along the headband 5 or crown 6 of the cap 1. Alternatively, the retainer 50, cantilever 56 or disk attachment point 57 may be affixed directly to the cap 1 by sewing, gluing, riveting or other attachment methods.

Referring now to FIGS. 9–11: In yet another embodiment of retainer assembly 20 for a cannula nosepiece 18 and supply tubes 11, 12, the retainer 20 comprises a pair of grooved triangular retainers 60 having rounded apexes which may similarly be affixed to the material 81 on the headband 5 or crown 6 of the cap 1. The rounded triangular retainers 60 are preferably constructed so as to retain supply tubes 11, 12 and a nasal cannula nosepiece 18 therebetween, and to be adjustable as to their location on the headband 5 or crown 6 of the cap 1. Each rounded triangular retainer 60 preferably comprises an arced structure 60 with a groove 64 therein, which is adapted to retain a cannula supply tube 11, 12 therein, while maintaining a bend in the tube 11, 12. In the embodiment of the retainer 60 of FIGS. 9–11, each rounded triangular retainer 60 comprises a block of material essentially shaped as a triangular prism, with the upward pointed apex being rounded. The retainer 60 may be constructed from wood, plastic, metal, leather, rubber, cardboard, foam rubber, resilient Styrofoam, polystyrene or any material sufficiently rigid to support the supply tubes 11, 12 and cannula nosepiece 18 therebetween. To maximize comfort to the wearer and provide a more secure attachment point to the cap 1, the rounded triangular retainers 60 are preferably constructed of a light and rigid material such as foam rubber, which is not only light, but also simplifies assembly because of the ability to easily fabricate a dowel using a punch. The thickness of the material is preferably between 0.2 to 0.5 inches to provide a light retainer 60. The rounded apex of the triangular retainer 60 preferably has an arc length and a radius of curvature sufficient to preclude kinking and blocking of a cannula tube 11, 12 supported thereby. The arc length may vary from between 0.5 inches to up to 3 inches, and the radius of curvature may be as few as 1 inch or as much as 10 inches. In the most preferred embodiment, the arc length is approximately 1.5 inches with a radius of curvature of 4 inches. The width of the rounded triangular retainer 60 is at least as wide as the diameter of a standard cannula tube 11, 12 and preferably at least twice as wide as the cannula tube 11, 12 diameter, or approximately 0.3–1.0 inches.

The rounded triangular retainer 60 also has a groove 64 along the top portion of the retainer 60, which is preferably located at the proximal portion of the retainer 60, but which may be centrally or anywhere along in the width dimension between the proximal 65 and distal 63 portions of the retainer 60. The depth of the groove 64 must be sufficient to retain a cannula tube 11, 12 therein. More preferably, the depth of the groove 64 is at least half the diameter of the cannula supply tube 11, 12 and up to 3 times the tube 11, 12 diameter, or approximately 0.1–0.4 inches.

Referring to FIGS. 9 and 10: In one embodiment of the invention, the rounded triangular retainers 60 are of unitary construction. However, in an alternate embodiment of invention, each rounded triangular retainer 60 may be constructed with modules (not shown) that are attached together. This may be accomplished using two rounded triangular portions having a first width, height, and circumference, and attaching the proximal 65 and distal 63 rounded triangular portions to the faces of a third rounded triangular portion 67 having a smaller height and circumference. This creates a modular rounded triangular retainer 60 having a first width, height, and circumference, and having a central groove 64 along the upper sides adjacent the rounded apex, wherein the groove 64 has a smaller height and circumference than the outer portions 65, 63 of the modular rounded triangular retainer 60.

Referring to FIGS. 9 and 11: In the preferred embodiment of the triangular retainers 60, the rounded triangular retainers 60 are of unitary construction. However, in an alternate embodiment of invention, each rounded triangular retainer 60 may be constructed with modules (not shown) that are attached together. This may be accomplished using a distal rounded triangular portion having a first width, height, and circumference, and attaching distal 63 rounded triangular portion to the face of a third rounded triangular portion 67 having a smaller height and circumference. This creates a modular rounded triangular retainer 60 having a first distal width, height, and circumference, and having a proximal groove 64 along the upper sides adjacent the rounded apex, wherein the groove 64 has a smaller height and circumference than the outer portion 63 of the modular rounded triangular retainer 60.

On the central part the proximal portion 65 or 67 of each rounded triangular retainer 60 is a connection point 61 for securing the retainer 60 to one face of a length of hook (or loop) fastener material 80. The connection point 61 is attached to the back face of the hook or loop material 80, i.e., the face of the material 80 opposite to the attachment point 61 of the retainer 80 has the hook or loop fasteners thereon. In FIGS. 9 and 10, this connection point 61 is shown as a flat disc 61 with a small cantilever 66 that connects at the central portion proximal portion 65 of the rounded triangular retainer 60. The attachment point 61 however may comprise shapes other than a disc, such as a square, and the cantilever 66 may be eliminated. With the cantilever 66 eliminated, the rounded triangular retainer 60 may be connected at more than one point to the disc 61. The attachment between the rounded triangular retainer 60, cantilever 66, disk 61 and fastener 80 may be accomplished by gluing, sewing, riveting, snaps or like attachment methods. FIG. 11 shows the preferred attachment method between the reatainer 60 and the fastener 80, wherein the fastener material 80 is attached directly (as by gluing) to the proximal grooved portion 67 of the retainer 60. This allows the retainer 60 and attached hook or loop fastener material 80 to be attached to the loop or hook material 81 along the headband 5 or crown 6 of the cap 1. Alternatively, the retainer 60, cantilever 66 or disk attachment point 61 may be affixed directly to the cap 1 by sewing, gluing, riveting or other attachment methods.

Referring now to FIGS. 2 and 3: The retainers 40, 50 and 60 described herein above are attached to an existing hat, cap, or other headgear 1 having essentially unitary headband 5 and crown portions 6. The crown portion 6 may have right, left, front and rear portions attached to the corresponding portions of the headband portion 5. In another embodiment of the invention, the headgear 2 comprises another adjustable types of headgear, having separate attachable headband 5 and crown portions 25. The headband 5 preferably comprises a length of adjustable material, such as a band cloth material, which may also be elasticized. For example the headband 5 may comprise a polyester and/or cotton cloth band with elastic band(s) woven therein. The headband 5 may also comprise a length of hook or loop fastener material. The headband 5 may be of unitary construction (circular), but preferably has a detachable, adjustable portion 51, 52 therein. More specifically, a length of elasticized material may be used having fasteners on opposing ends 51, 52 thereof. More specifically, a first end 51 of the band may have hook fasteners on the outside face, and on the opposing end 52 loop fasteners on the inside face, such that the hook and loop fasteners are in mating/engageable relationship. Alternatively, hook and loop fasteners may be used on the opposite ends 51, 52, or opposite faces, or both to provide a wide range of engageability. The headband 5 most preferably comprises a length of loop fastener material, having a portion of hook fastener material affixed to the inside face of one opposing end 51 or 52 thereof for engagement with the opposite end 52 or 51 thereof. Furthermore, other means for engaging the ends 51, 52 of the headband 5 to each other may include snaps, buttons, buckles, cord and eyelet, or other types of fasteners. This provides a headband portion 5 that is not only elasticized to fit snugly about the head, but also has fasteners to provide a headband 5 that fits a variety of head sizes.

Referring again to FIG. 3: The headgear 2 also comprises a crown portion 25 that is engageable with the headband portion 5. The crown portion 25 comprises crown band 25 made from a length of adjustable material, such as a band cloth material, which further may be elasticized. For example the crown band 25 may comprise a polyester and/or cotton cloth band with elastic band(s) woven therein. The crown band 25 is preferably adjustably engageable with and detachable from the headband portion 5. More specifically, a length of elasticized material may be used for the crown band 25 having fasteners 36 on opposing ends 26, 27 thereof, engageable with complimentary fasteners 32 on some or all of the headband 5. More specifically, each end 26, 27 of the crown band 25 may have hook fasteners 36 on the inside face thereof engageable with loop fasteners 32 on the outside faces of the headband 5, such that the hook and loop fasteners 36, 32 are in mating, engageable relationship. The fasteners 32 on the headband 5 may cover the majority of the outside surface of the headband 5, or may extend along only the front and sides of the headband 5, to at least above the portion of the headband 5 to be situated above the ears. This provides a great number of attachment points for the ends 26, 27 of the crown band 25 to be adjustably engaged with the headband 5.

Alternatively, the crown band 25 may have loop fasteners 36 thereon, and the headband 5 may have hook fasteners 32 thereon. The hook and loop fasteners 32, 36 may be used on the opposite ends, or opposite faces of the crown band 25, or both to provide a wide range of engageability. Furthermore, other means for engaging the ends 26, 27 of the crown band 25 to the headband 5 may include snaps, buttons, buckles, cord and eyelet, or other types of fasteners 36. This provides a crown band portion 25 that is not only elasticized to fit snugly over the head and prevent slippage of the headband 5, but also has fasteners 36 to provide a crown band 25 that fits a variety of head sizes.

In the preferred embodiment of the invention, the crown band portion 26 is affixed to the headband portion 5 above or in front of the user's ears. However, in alternate embodiments (not shown), the crown band 25 portion may be aligned parallel to a plane between the user's ears. Alternatively, the crown band 25 may be affixed and aligned perpendicular to a plane between the user's ears, or at any angle to the plane that provides a secure attachment and retention of the headgear 2 on the user's head.

Referring now to FIGS. 2-3 and FIGS. 4-11: The headgear 2, comprising a headband portion 5 and crown band portion 25) are adapted for affixing a pair of cannula retainers 20 thereto. Specifically, a pair of cannula retainers 20 of the types 40, 50, 60 shown in FIGS. 4-11, are adapted to be adjustably affixed to the crown portion 25 and/or headband portion 5 of the headgear 2. In the preferred embodiment of the invention, the crown band 25 is affixed with hook type fasteners 36 to the loop type fasteners 32 on the portion of the headband 5 adjacent the user's ears. The cannula retainers 20, (i.e., dowels 40, arced retainers 50, or rounded triangular retainers 60) each are backed by a length of hook type fasteners 80. The outside faces of both the crown portion 25 and headband portion 5 have exposed loop type fasteners 37, 32 thereon for affixing the hook fasteners 80 of the retainers 20 thereto. Thus, the hook fasteners 80 on the retainers 20 may be affixed to loop fasteners 32, 37 on any portion of the headband 5 or the crown band 25.

In yet another alternative embodiment of the invention, the exposed surfaces of the headband 5 and crown band 20 may have hook type fasteners 32, 37 thereon, and the cannula retainers 20 may have loop fasteners 80 thereon, for affixing to the hook fasteners 32 of the headband and/or the hook fastener 37 of the crown band 25. In yet another embodiment, the cannula retainers 20 may be permanently affixed to the outer faces of the ends 26, 27 of the crown band 25, by means of sewing, glue, snaps, grommets, rivets or the like.

Thus, the present invention provides a cannula retention apparatus comprising an article of headgear 1, 2 having retainers 20 adjustably affixed thereon for retention of cannula supply tubes 11, 12. The retainers 20 have rounded upper surfaces with grooves therein adapted for placement and retention of cannula supply tubes 11, 12. The supply tubes 11, 12 may tend from the nasal cannula nosepiece 18 to the front of each retainer 20, into the groove and then tend downwardly from the back of each retainer 20 to the cannula tube junction 14 below the user's chin. Alternately, for additional security of retention of the supply tubes 11, 12, the tubes may tend upwardly from the nasal cannula nosepiece 18 to the back portion of the retainers 20, through the groove in each retainer 20, and then tend downwardly from the front of each retainer 20 to the cannula tube junction 14 below the user's chin. This placement of the cannula tubes 11, 12 provides a more secure retention because the downward tending portion of the tube 11, 12 contacts the upward tending portion of the tube 11, 12, and the friction of their mutual contact prevents the tubes 11, 12 from sliding in the grooves.

The head gear 1, 2 is preferably adjustable to provide a proper fit to the user's head. The retainers 20 are also preferably adjustable to allow their placement in the most comfortable position with relation to the cannula tubes 11, 12 and the user's ears and face. This prevents the positioning of the tubes 11, 12 on the ears and face of the user, which is uncomfortable and is more prone to falling off the user's face. Additionally, the positioning off the ears and face prevents chaffing and pain, as well as dislocation of the tubes 11, 12 and cannula nosepiece 18 due to body movement of the patient, i.e., when walking or during sleep.

While the above description contains many specificities, these should not be construed as limitations on the scope of the invention, but rather as exemplification of preferred embodiments thereof. Many other variations are possible, for example:

While in the preferred embodiment of the invention the headgear comprises either a cap or an adjustable headband and crownband, many other types of headgear including helmets, western hats, surgical caps, ski hats; hospital caps; golf caps; tennis caps; fishing hats; western hats; men's and women's dress hats, derbies; fedoras; bonnets; helmets; construction hard hats; straw hats; visor-less caps; berets; winter hats; and practically any type of headgear may be used;

The headgear may be constructed from a variety of materials including cotton, polyester, cotton/poly blends, elasticized material, lycra, silk, felt, leather, plastic, paper, straw and any variety of materials used in making hats;

The headgear may comprise a headband and a crown portion, simply a headband, or a headband and one crown band, or multiple crown bands;

The retainers may comprise grooved cylinders, arcs, rounded triangles, rounded squares, or a variety of other rounded polygonal prisms with grooves in the rounded upper surfaces thereof;

The retainers may be constructed from wood, plastic, metal, leather, rubber, cardboard, foam rubber, polystyrene, resilient Styrofoam or any material sufficiently rigid to support the supply tubes and cannula;

The fasteners for the headband, crown band, and/or retainers may comprise snaps, grommets, hook and eye, hook and loop, laces, buckles, glue, rivets, sewing, or any other known means of attachment, either permanent or detachable.

I claim:

1. A nasal cannula retention apparatus comprising:
   an article of headgear comprising;
   a substantially circular headband portion having left and right sides;
      said headband portion having a first length of loop fastener material attached to said left and right sides;
   a crown band having left and right ends, and interior and exterior faces;
      said left end of said crown band having a first length of hook fastener material attached to said interior face;
      said right end of said crown band having a second length of hook fastener material attached to said interior face;
      said left end of said crown band having a first length of loop fastener material attached to said exterior face;
      said right end of said crown band having a second length of loop fastener material attached to said exterior face;
   a first substantially cylindrical dowel portion having a proximal face and a distal face and a rounded upper surface;
      said rounded upper surface having a first recessed groove therein, adapted to retain a portion of a cannula supply tube therein;
      said proximal face of said first substantially cylindrical dowel portion having a first length of hook fastener material attached thereto; and
   a second substantially cylindrical dowel portion having a proximal face and a distal face and a rounded upper surface;
      said rounded upper surface having a second recessed groove therein, adapted to retain a portion of a cannula supply tube therein;
      said proximal face of said second substantially cylindrical dowel portion having a second length of hook fastener material attached thereto;
   wherein said first and second lengths hook fastener material on said interior faces of said left and right ends of said crown band are detachably engageable with said first length of loop fastener material attached to said left and right sides of said headband portion;
   and wherein said first length of hook fastener material attached to said proximal face of said first cannula supply tube retainer is detachably engageable with either said first length of loop fastener material on said headband portion or said first length of loop fastener material attached to said exterior face of said left end of said crown band; and
   and wherein said second length of hook fastener material attached to said proximal face of said second cannula supply tube retainer is detachably engageable with either said first length of loop fastener material on said headband portion or said second length of loop fastener material attached to said exterior face of said right end of said crown band.

2. The nasal cannula retention apparatus of claim 1, wherein said first or second cannula supply tube retainer further comprises:
   a distal portion, a proximal portion, and a central portion;
      said distal portion and said proximal portion each having circular cross-sections having a first radius;
      said central portion having a circular cross-section having a second radius smaller than said first radius.

3. The nasal cannula retention apparatus of claim 1, wherein said first or second cannula supply tube retainer further comprises:
   a distal portion, and a proximal portion;
      said distal portion having a circular cross-section having a first radius;
      said proximal portion having a circular cross-section having a second radius smaller than said first radius.

4. A nasal cannula retention apparatus, comprising:
   an article of headgear comprising;
   a substantially circular headband portion having left and right sides; and
   a crown portion having left and right sides;
      said left side of said crown portion being connected to at least a portion of said left side of said headband portion;
      said right side of said crown portion being connected to at least a portion of said right side of said headband portion;

a first cannula supply tube retainer comprising a first substantially cylindrical dowel comprising a distal portion, a proximal portion, and a central portion, and having a proximal face;
   said distal portion and said proximal portion each having circular cross-sections having a first radius;
   said central portion having a circular cross-section having a second radius smaller than said first radius;
   said central portion being adapted to retain a portion of a cannula supply tube therein;
   said proximal face of said first cannula supply tube retainer being attached to said left side of said headband portion or said crown portion; and
a second cannula supply tube retainer comprising a second substantially cylindrical dowel comprising a distal portion, a proximal portion, and a central portion, and having a proximal face;
   said distal portion and said proximal portion each having circular cross-sections having a first radius;
   said central portion having a circular cross-section having a second radius smaller than said first radius;
   said central portion being adapted to retain a portion of a cannula supply tube therein;
   said proximal face of said second cannula supply tube retainer being attached to said right side of said headband portion or said crown portion.

5. The nasal cannula retention apparatus of claim 4:
wherein said first cannula supply tube retainer is attached to said left side of said headband portion using a first fastener;
and wherein said second cannula supply tube retainer is attached to said right side of said headband portion using a second fastener.

6. The nasal cannula retention apparatus of claim 5, wherein said first and second fasteners further comprise:
   a first length of loop fastener material attached to said left and right sides of said headband portion;
   a first length of hook fastener material attached to said proximal face of said first cannula supply tube retainer;
      said first length of hook fastener material being detachably engageable with said first length of loop fastener material; and
   a second length of hook fastener material attached to said proximal face of said second cannula supply tube retainer;
      said second length of hook fastener material being detachably engageable with said first length of loop fastener material.

7. The nasal cannula retention apparatus of claim 5, wherein said first and second fasteners further comprise:
   a first length of hook fastener material attached to said left and right sides of said headband portion;
   a first length of loop fastener material attached to said proximal face of said first cannula supply tube retainer;
      said first length of loop fastener material being detachably engageable with said first length of hook fastener material; and
   a second length of loop fastener material attached to said proximal face of said second cannula supply tube retainer;
      said second length of loop fastener material being detachably engageable with said first length of hook fastener material.

8. The nasal cannula retention apparatus of claim 4, wherein said crown portion of said headgear comprises:
   a crown band having left and right ends, and interior and exterior faces;
   a first length of hook fastener material attached to said interior face of said left end of said crown band;
   a second length of hook fastener material attached to said interior face of said right end of said crown band;
   a first length of loop fastener material attached to said exterior face of said left end of said crown band; and
   a second length of loop fastener material attached to said exterior face of said right end of said crown band;
   wherein said first and second lengths hook fastener material on said interior faces of said left and right ends of said crown band are detachably engageable with said first length of loop fastener material attached to said left and right sides of said headband portion;
   and wherein a first length of hook fastener material is attached to said proximal face of said first cannula supply tube retainer;
      said first length of hook fastener material being detachably engageable with either said first length of loop fastener material on said headband portion or said first length of loop fastener material attached to said exterior face of said left end of said crown band; and
   and wherein a second length of hook fastener material attached to said proximal face of said second cannula supply tube retainer;
      said second length of hook fastener material being detachably engageable with either said first length of loop fastener material on said headband portion or said second length of loop fastener material attached to said exterior face of said right end of said crown band.

9. The nasal cannula retention apparatus of claim 4, wherein the material of construction of said first and second cannula supply tube retainers is selected from the group comprising: wood, plastic, metal, leather, rubber, cardboard, foam rubber, resilient Styrofoam, and polystyrene.

10. The nasal cannula retention apparatus of claim 4, wherein the materials of construction of said headband or said crown portion are elasticized.

11. The nasal cannula retention apparatus of claim 4, wherein said article of headgear further comprises a visor attached to a front portion said headband portion.

12. A nasal cannula retention apparatus, comprising:
   an article of headgear comprising;
      a substantially circular headband portion having left and right sides; and
      a crown portion having left and right sides;
         said left side of said crown portion being connected to at least a portion of said left side of said headband portion;
         said right side of said crown portion being connected to at least a portion of said right side of said headband portion;
   first and second cannula supply tube retainers, each comprising a first substantially cylindrical dowel comprising a distal portion, and a proximal portion;
      said distal portion having a circular cross-section having a first radius;
      said proximal portion having a circular cross-section having a second radius smaller than said first radius;
      said proximal portion being adapted to retain a portion of a cannula supply tube therein;
      said proximal faces of said first and second cannula supply tube retainers being attached to said left and right sides of said headband portion or said crown portion.

13. A nasal cannula retention apparatus, comprising:
   an article of headgear comprising;

a substantially circular headband portion having left and right sides; and a crown portion having left and right sides;
- said left side of said crown portion being connected to at least a portion of said left side of said headband portion;
- said right side of said crown portion being connected to at least a portion of said right side of said headband portion; and first and second cannula supply tube retainers, each comprising a substantially triangular prism having a rounded apex and comprising a distal portion, a proximal portion, and a central portion;
- said distal portion and said proximal portion each having a first height, a first apex arc length and a first apex radius of curvature;
- said central portion having second height smaller than said first height;
- said central portion having second apex arc length smaller than said first apex arc length;
- said central portion having second apex radius of curvature smaller than said first apex radius of curvature.

14. A nasal cannula retention apparatus, comprising:

an article of headgear comprising;

a substantially circular headband portion having left and right sides; and a crown portion having left and right sides;
- said left side of said crown portion being connected to at least a portion of said left side of said headband portion;
- said right side of said crown portion being connected to at least a portion of said right side of said headband portion; and first and second cannula supply tube retainers, each comprising a substantially triangular prism having a rounded apex and comprising a distal portion, and a proximal portion;
- said distal portion having a first height, a first apex arc length and a first apex radius of curvature;
- said proximal portion having second height smaller than said first height;
- said proximal portion having second apex arc length smaller than said first apex arc length;
- said proximal portion having second apex radius of curvature smaller than said first apex radius of curvature.

* * * * *